United States Patent
Bombardelli et al.

(10) Patent No.: US 7,153,884 B2
(45) Date of Patent: Dec. 26, 2006

(54) C-2' METHYLATED DERIVATIVES OF PACLITAXEL FOR USE AS ANTITUMOUR AGENTS

(75) Inventors: Ezio Bombardelli, Milan (IT); Gabriele Fontana, Milan (IT); Arturo Battaglia, Bologna (IT); Samanta Cimitan, Ponte di Pieve (IT)

(73) Assignee: Indena S.p.A., Milan (IT)

( * ) Notice: Subject to any disclaimer, the term of this patent is extended or adjusted under 35 U.S.C. 154(b) by 328 days.

(21) Appl. No.: 10/485,982

(22) PCT Filed: Jul. 23, 2002

(86) PCT No.: PCT/EP02/08185

§ 371 (c)(1),
(2), (4) Date: Jul. 22, 2004

(87) PCT Pub. No.: WO03/013503

PCT Pub. Date: Feb. 20, 2003

(65) Prior Publication Data

US 2004/0242674 A1    Dec. 2, 2004

(30) Foreign Application Priority Data

Aug. 7, 2001    (IT) .......................... MI2001A1734

(51) Int. Cl.
*A61K 31/337* (2006.01)
*A61K 31/381* (2006.01)
*C07D 305/14* (2006.01)
*C07D 407/10* (2006.01)
*C07D 409/10* (2006.01)

(52) U.S. Cl. ...................... 514/444; 514/449; 549/60; 549/472; 549/510

(58) Field of Classification Search ................ 514/444, 514/449, 471; 549/60, 472, 510
See application file for complete search history.

(56) References Cited

OTHER PUBLICATIONS

Kant et al., "Diastereoselective addition of Grignard reagents to azetidine-2-,3-dione: synthesis of novel Taxol analogues" Tetrahedron Letters, vol. 37, No. 36, 1996, pp. 6495-6498 XP002216532.
Chen et al., "Novel C-4 Paclitaxel (Taxel) Analogs: Potent Antitumor Agents" Bioorganic & Medicinal Chemistry Letters, Oxford, GB, vol. 5, No. 22, 1995, pp. 2741-2746, XP001025908 ISSN: 0960-894X.
Chen et al., "Paclitaxel (Taxol) Chemistry and Structure—Activity Relationship" Chemistry and Pharmacology of Taxol and its Derivatives, XX, XX, NR. 22, pp. 165-253 XP008005396 (1995).

*Primary Examiner*—Taofiq Solola
(74) *Attorney, Agent, or Firm*—Young & Thompson

(57) ABSTRACT

Taxane derivatives of formula (I) in which: R is trifluoromethyl, phenyl, 2-furyl, 2-thienyl; $R^1$ is t-butoxycarbonyl or benzoyl; $R_2$ is hydroxy; $R_3$ is hydrogen or, together with $R_2$, it forms the residue of a cyclic carbonate of formula: II with the proviso that when R3 is hydrogen, R is different from phenyl. Compounds of formula (I) have antitumor activity

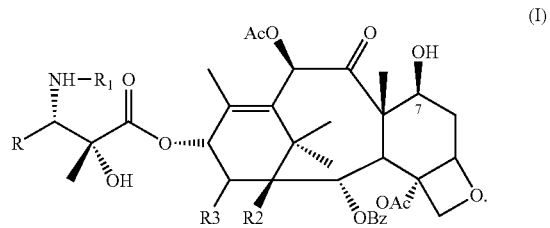

4 Claims, No Drawings

C-2' METHYLATED DERIVATIVES OF PACLITAXEL FOR USE AS ANTITUMOUR AGENTS

The present invention relates to novel taxane derivatives having antitumor activity and to the processes for the preparation thereof.

More particularly, the present invention relates to the compounds of formula (I):

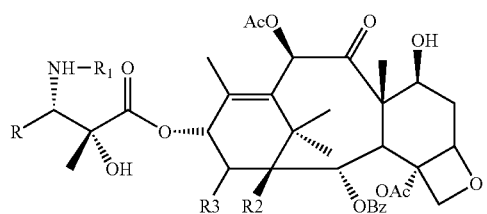

in which:
R is trifluoromethyl, phenyl, 2-furyl, 2-thienyl;
$R^1$ is t-butoxycarbonyl or benzoyl;
$R_2$ is hydroxy;
$R_3$ is hydrogen or, together with $R_2$, it forms the residue of a cyclic carbonate of formula:

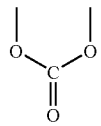

with the proviso that when $R_3$ is hydrogen, R is different from phenyl.

Compounds of formula (I) are derivatives of paclitaxel or of docetaxel, known drugs having antitumor activity.

Compounds of formula (I) wherein $R_3$ is hydrogen and R is phenyl are described by Greene et al. in J. Chem. Soc. Perkin Trans.1, 1995, pp 1811–1815. Paclitaxel derivatives bearing a C-2'-methylated (2R,3S) side-chain are disclosed by Kant et al. in Tetrahedron, vol. 37, n. 36, pp 6495–6498, 1996. Kant has demonstrated that this structural modification induces a significant response enhancement in comparison with the parent compound paclitaxel in certain tests (inhibition of microtubule depolymerization), due to better binding affinity to microtubules and better cytotoxicity toward KBVI. In addition, some of these taxanes synthesized from 14β-hydroxybaccatin 1,14-carbonate had improved water solubility. Finally, one of these taxanes contains a trifluoromethyl substituent at the C-3 position in order to block the metabolic pathways associated with the cytochrome P-450 class of enzymes. The improved pharmacological characteristics of these new compounds may well be related to the modification of the activity spectrum against various cancer types.

Preferred compounds of the invention are the following:
(2'R,3'R)-13-[N-benzoyl-3-(2-furyl)-2-methyl-isoserinoyl]-baccatin III;
(2'R,3'R)-13-[N-t-butoxycarbonyl-3-(2-furyl)-2-methyl-isoserinoyl]-baccatin III;
(2'R,3'S)-13-[N-t-butoxycarbonyl-3-phenyl-2-methyl-isoserinoyl]-14β-hydroxybaccatin III 1,14-carbonate;
(2'R,3'R)-13-[N-t-butoxycarbonyl-3-trifluoromethyl-2-methyl-isoserinoyl]-14β-hydroxybaccatin III 1,14-carbonate;
(2'R,3'R)-13-[N-t-butoxycarbonyl-3-(2-furyl)-2-methyl-isoserinoyl]-14β-hydroxybaccatin III 1,14-carbonate.
(2'R,3'R)-13-[N-t-butoxycarbonyl-3-(2-thienyl)-2-methyl-isoserinoyl]-14-hydroxybaccatin III 1,14-carbonate.

The compounds of formula (I) are prepared by reaction of a compound of formula (II)

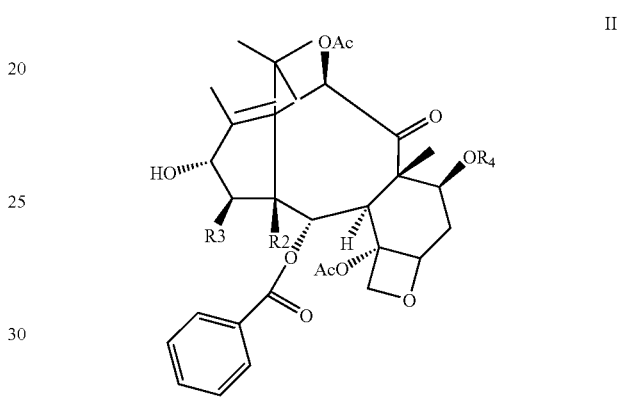

in which $R_2$ and $R_3$ are as defined above, and $R_4$ is a protecting group, preferably triethylsilyl, with a compound of formula (III)

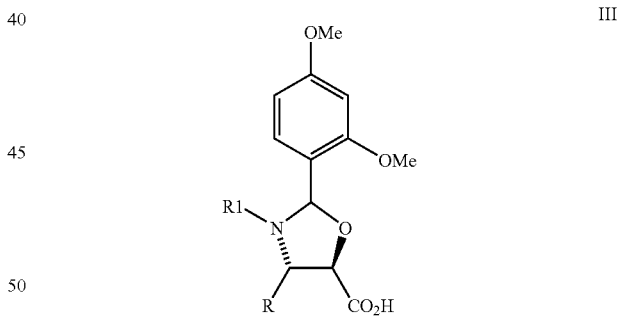

wherein R and $R_1$ are as defined above.

Compound of formula (III) can be prepared from the corresponding alkyl esters, in particular from the methyl ester, known from Tetrahedron Asymm. 2001, 12, 1015–1027 and J. Chem. Soc. Perkin Trans.1 1995, 1811–1816, by hydrolysis in alcoholic solvents. The resulting acid, without being isolated, can be directly condensed with the baccatin III derivative of formula (II), in the presence of a suitable condensing agent, for example di-2-pyridyl thionocarbonate and dimethylaminopyridine in a suitable solvent. The hydroxy-protecting group at the 7-position is removed to afford the desired compounds of formula (I).

Alternatively, compounds of formula (II) can be reacted with compounds of formula (IV)

wherein R is as defined above.

Compound of formula (IV) in which R is phenyl is described in J. Org. Chem. 1991, 56, 1681–1684; Tetrahedron, 1992, 48, 6585–7012, EP 400971, U.S. Pat. No. 5,175, 315.

Compound of formula (IV) in which R is trifluoromethyl can be prepared according to the following scheme

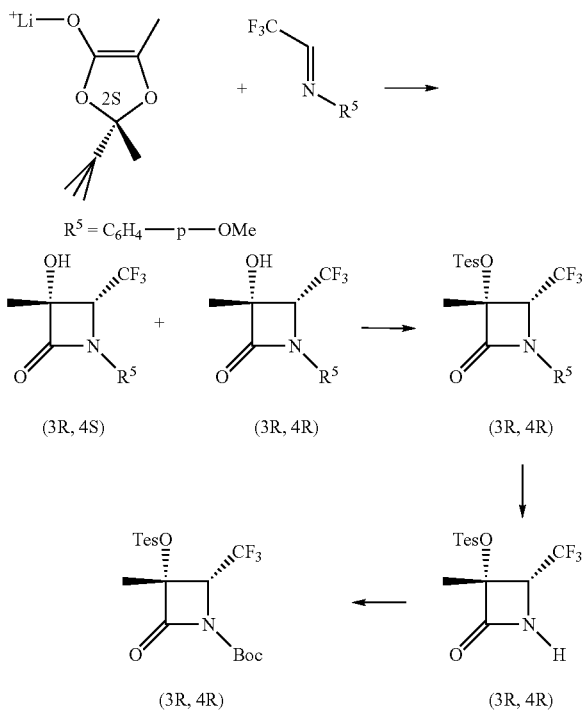

Compound of formula (IV) in which $R_1$ is 2-furyl can be prepared starting from (3R,4R)-4-(furan-2-yl)-3-hydroxy-3-methyl-azetidin-2-one, known from J. Org. Chem. 1999, 64, 4643, 4651, according to the following scheme:

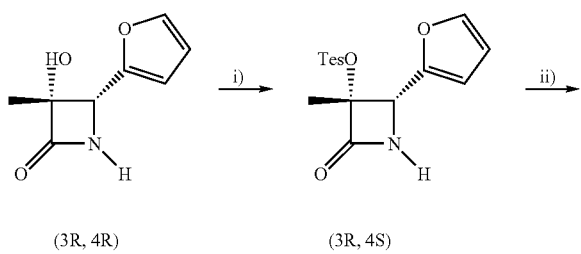

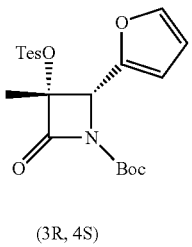

i): TesCl/DMF/25° C.; ii) Boc₂O/Et₃N/DMAP/0° C. to 25° C.

Compounds of formula (II) are known from J. Med. Chem. 1997, 40, 267–278.

The reaction between compound (II) and compound (IV) is carried out in aprotic solvents under inert atmosphere.

Typically, the reaction is carried out at a temperature of about −40° C. −5° C. in the presence of sodium hexamethyldisilazane. The hydroxy-protecting group at 7 is then removed to afford compounds (I).

The compounds of the present invention have shown strong antitumor activity against cancer cells of the breast, lung, ovary, colon, prostate, kidney, pancreas, as well as against cells resistant to known anticancer drugs such as adriamycin, vinblastine and platinum derivatives.

Therefore, the invention is directed to pharmaceutical formulations containing an effective amount of a compound of the invention, together with pharmacologically acceptable carriers and excipients. More particularly, the compounds can be formulated in the form of tablet, powder, granulate, capsule, injectable solution, suppository, emulsion, dispersion, and the like. For the intravenous administration, mixtures of Chremophor L and ethanol, polysorbate and ethanol or liposome preparations prepared with natural or synthetic phosphatidylcholine, or mixtures of natural phospholipids in the presence of cholesterol, are preferably used; for the oral administration, soft-gelatin capsules are preferably prepared in which the product is solubilised in polysorbates, PEG or mixtures thereof, optionally in the presence of phospholipids. Compounds (I) can be administered to humans at concentrations ranging from 50 to 500 mg/m².

The following examples illustrate the invention in greater detail.

The abbreviations used are as follows:
TES=triethylsilyl; DMF=dimethylformamide; DMAP=(N,N-dimethylamino)pyridine; NaHMDS=sodium hexamethyldisilazide; LiHMDS=lithium hexamethyldisilazide; THF=tetrahydrofuran; HMPA=hexamethylphosphoric triamide.

EXAMPLE 1

(4S,5R)-3-Benzoyl-2-(2,4-dimethoxyphenyl)-4-(furan-2-yl)-5-methyl-oxazolidine-5-carboxylic acid methyl ester (0.128 g, 0.285 mmol) in methanol was stirred with K₂CO₃ (2 eq) at 25° C. for 24 h in anhydrous medium. The reaction mixture was concentrated in vacuo, diluted with a saturated NH₄Cl solution and extracted with ethyl acetate. The aqueous phase was acidified to pH 4 with 5% NaHSO₄ and extracted with ethyl acetate. The organic phase was dried and the solvent was evaporated off. The residue (1 eq) was added to a toluene solution of 7-TES-baccatin III (0.04 g, 0.057 mmol) in the presence of di-2-pyridyl thionocarbonate (1 eq) and dimethylaminopyridine (0.5 eq) at 20° C. under argon atmosphere. The reaction mixture was heated at 60° C. for 80 hours with stirring. After addition of ethyl acetate, the reaction mixture was extracted with brine. The organic phase was washed with brine, then dried and evaporated. Chromatography (SiO$_2$, ethyl acetate/n-hexane, 1:1) afforded (2'R,3'R)-13-[N-benzoyl-N,O-(2,4-dimethoxybenzyliden)-3-(2-furanyl)-2-methylisoserinoyl]-7-TES-baccatin III (0.023 g, 2.28 mmol, 40%). The compound has the following characteristics:

$^1$H NMR (CDCl$_3$): δ=0.61 (m, 6H, 3CH$_2$), 0.95 (t, 9H, 3Me), 1.22 (s, 3H, Me), 1.27 (s, 3H, Me), 1.68 (s, 3H, Me), 1.89 (m, 1H of C6-H), 2.10–2.25 (m, 2H of C14-H), 2.21 (s, 3H, Me), 2.24 (s, 3H, Me), 2.33 (s, 3H, Me), 2.50 (m, 1H of C6-H), 2.65 (s, 3H, Me, OAc of C-4), 3.90–4.0 (m, 8H, 6H of 2 Me, 1H of C3-H, and 1H of OH), 4.12 (d, 1H, of C20-H, J=8.0 Hz), 4.32 (d, 1H, C20-H), 4.58 (m, 1H of C7-H, J$_1$=5.8 Hz, J$_2$=10.2 Hz,), 4.95 (dd, 1H of C5-H, J$_1$=1.5 Hz, J$_2$=9.6 Hz), 5.55 (b, 1H of C3'-H), 5.70 (d, 1H of C2-H, J=5.7 Hz), 6.30–6.40 (m, 2H), 6.40–6.50 (m, 3H), 6.54 (s, 1H), 6.82 (s, 1H), 7.20–7.40 (m, 5H, arom), 7.40–7.50 (m, 3H, arom), 7.54–7.60 (m, 1H, arom), 8.04–8.07 (m, 2H, arom).

This compound (0.023 g, 2.28 mmol) was dissolved in CH$_2$Cl$_2$ (3.0 ml) and treated with a solution (100 μl) of acetyl chloride in methanol (70 μl of acyl chloride in 10 ml of MeOH) at 25° C. After 7 hrs, the reaction mixture was extracted with H$_2$O. The organic solvent was dried and evaporated. The residue was chromatographed (SiO$_2$, n-hexane/ethyl acetate, 1:1) to afford 0.019 g (0.022 mmol, 98%) of (2'R,3'R)-3'-dephenyl-3'-(2-furyl)-2'-methyl-paclitaxel.

The compound has the following characteristics:

$^1$H NMR (CDCl$_3$): δ=1.13 (s, 3H, Me), 1.23 (s, 3H, Me), 1.55 (s, 3H, Me), 1.70 (s, 3H, Me), 1.81 (s, 3H, Me), 1.89 (m, 1H, H-6β), 2.07 (m, 1H of C14-H), 2.24 (s, 3H, Me), 2.40 (m, 1H of C14-H), 2.49 (d, 1H, OH of C7-H), 2.55 (m, 1H of C6-H), 2.65 (s, 3H, Me), 3.75 (s, 1H, OH), 3.82 (d, 1H of C3-H, J=7.2 Hz), 4.21 (d, 1H of C20-H J=8.4 Hz), 4.31 (d, 1H of C20-H), 4.40 (m, 1H of C7-H), 4.95 (dd, 1H of C5-H, J$_1$=1.5 Hz, J$_2$=9.6 Hz), 5.66 (d, 1H of C2-H), 5.79 (d, 1H, of C3'-H, J=9.5 Hz), 6.26.(s, 1H of C10-H), 6.30 (m, 1H of C13-H), 6.41 (m, 2H, 2-furyl), 7.12 (d, 1H, NH), 7.33 (m, 2H, arom), 7.44 (m, 1H, 2-furyl), 7.46 (m, 1H, arom), 7.52 (m, 2H, arom), 7.60 (m, 1H, arom), 7.67 (m, 2H, arom), 8.19 (m, 2H, arom).

EXAMPLE 2

The coupling of (4S,5R)-N-Boc-N,O-(2,4-dimethoxybenzyliden)-3-phenyl-2-methylisosene methyl ester (J. Chem. Soc. Perkin Trans. 1995, 1811–1816) (0.154 g, 0.336 mmol) with 7-TES-baccatin III 1,14-carbonate[1] (0.05 g, 0.067 mmol) according to procedure described in example 1 afforded 0.021 g (0.023 mmol, 34%) of (2'R,3'S)-13-(N-Boc-2-methyl-3-phenylisoserinoyl)-14β-hydroxybaccatin III 1,14-carbonate.

The compound has the following characteristics:

$^1$H NMR (CDCl$_3$): δ=1.28 (s, 9H, 3Me of t-Boc), 1.30 (s, 3H, Me of C-15), 1.38 (s, 3H, Me of C-15), 1.41 (s, 3H, Me of C2'), 1.73 (s, 3H, Me of C-8), 1.84 (s, 3H, Me of C-12), 1.92 (m, 1H of C6-H), 2,26 (s, 3H, Me, OAc of C-10), 2.36 (b, 1H, OH), 2.56 (m, 1H of C6-H), 2.69 (s, 3H, Me, OAc of C-4), 3.52–3.55 (b, 1H, OH), 3.73 (d, 1H of C3-H, J=7.3 Hz), 4.25 (d, 1H of C20-H, J=8.5 Hz), 4.31 (d, 1H, of C20-H), 4.38 (m, 1H of C7-H), 4.85 (d, 1H of C14-H, J=7.1 Hz), 4.95 (dd, 1H of C5-H, J$_1$=2.4 Hz, J$_2$=9.6 Hz), 5.09 (d, 1H of C3'-H), 5.57 (d, 1H, NH, J=10.0 Hz), 6.13 (d, 1H, of C2-H), 6,27 (s, 1H of C10-H), 6.36 (m, 1H of C13-H), 7.30–7.40 (m, 5H,.arom), 7.48 (m, 2H, arom), 7.59 (m, 1H, arom), 8.04 (m, 2H, arom).

EXAMPLE 3 a) (3R,4S)-3.-triethylsilyloxy-4-(furan-2-yl)-3-methyl-azetidinone

Triethyl silyl chloride (0.316 g, 2.1 mmol) and imidazole (0.100 g, 1.5 mmol) were added to a stirred solution of (3R,4R)-4-(furan-2-yl)-3-hydroxy-3-methyl-azetidin-2-one (0.167 g, 1.0 mmol) in DMF (6.0 ml) at 25° C. under argon atmosphere. The reaction solution was quenched after 4 h with a saturated NH$_4$Cl aqueous solution and extracted with ethyl acetate. The organic phase was dried and concentrated under reduced pressure. Chromatography of the residue (SiO$_2$, ethyl acetate/n-pentane, 1:2) afforded 0.190 g (0.67 mmol 67%) of (3R,4S)-4-(furan-2-yl)-3-triethylsilyloxy-3-methyl-azetidin-2-one: $[\alpha]_D^{20}$=+42.8 (c 1.04, CHCl$_3$); IR (CDCl$_3$, cm$^{-1}$): 3600–3000, 3413, 2957, 1768, 1458, 1377, 1012; $^1$H NMR (CDCl$_3$): δ=0.65 (m, 6H, 3 CH$_2$), 0.95 (t, 9H, 3 Me), 1.19 (s, 3H, Me), 4.54 (s, 1H), 6.27 (d, 1H, 2-furyl), 6.28 (m, 1H, 2-furyl), 6.72 (b, 1H, NH), 7.40 (m, 1H, 2-furyl); $^{13}$H NMR (CDCl$_3$): δ=5.71 (CH$_2$), 6.73 (Me), 19.3 (Me), 61.0 (CH), 89.1(C), 108.1 (CH), 110.5 (CH), 142.7 (CH), 150.9 (C), 171.5 (C).

b) (3R,4S)-1-tert-butoxycarbonyl-3-triethylsilyloxy-4-(furan-2-yl)-3-methyl-azetidinone A solution of the derivative from the previous step (0.060 g, 0.21 mmol), DMAP (0.010 g), and triethylamine (88 μl, 0.63 mmol) in CH$_2$Cl$_2$ (3.0 ml) at 0° C. was added with a solution of di-tert-butyl-dicarbonate (121 ml, 0.52 mmol) in CH$_2$Cl$_2$ (1.0 ml). The reaction mixture was stirred at 25° C. for 1 h, then quenched with saturated NH$_4$Cl. The mixture was extracted with ethyl acetate and the organic layer was washed with brine, dried and concentrated under reduced pressure. Chromatography (SiO$_2$, n-pentane/ethyl acetate, 8:2) afforded 0.077 g (0.020 mmol, 97%) of (3R,4S)-1-tert-butoxycarbonyl-3-triethylsilyloxy-4-(furan-2-yl)-3-methyl-azetidinone:

$[\alpha]_D^{20}$ =+26.6 (c 0.98, CHCl$_3$); IR (CDCl$_3$, cm$^{-1}$): 2958, 1813, 1726, 1327, 1152; $^1$H NMR (CDCl$_3$): δ=0.54 (m, 6H, 3CH$_2$), 0.80 (t, 9H, 3Me), 1.41 (s, 9H, 3Me), 1.61 (s, 3H, Me), 4.73 (s, 1H), 6.27 (d, 1H, 2-furyl), 6.34 (m, 1.H, 2-furyl), 7.37 (m, 1H, 2-furyl); 3H NMR (CDCl$_3$): δ=5.6 (CH$_2$), 6.5 (Me), 23.0 (Me), 27.8 (3 Me), 62.7 (CH), 83.3 (C), 85.4 (C), 108.9 (CH), 110.3 (CH), 142.4 (CH), 147.9 (C), 148.7 (C), 167.7 (C).

c) (2'R,3'R)-13-[N-Boc-2-methyl-3-(2-furanyl)-isoserinoyl]-baccatin III

The β-lactam from step b) (0.082 g, 0.214 mmol) and 7-TES-baccatin III (0.060 g, 0.086 mmol) were dissolved in THF under argon atmosphere. The solution was cooled to −45° C. NaHMDS (solution 1.0 M in n-hexane, 2.5 eq) was added drop by drop with stirring. The temperature was raised to −20° C. in four hours. The reaction was quenched with saturated NH$_4$Cl; the mixture was extracted with ethyl acetate and dried. After evaporation of the solvent, the crude was purified by chromatography. The reaction product was dissolved at 0° C. in 1:1 MeCN/pyridine solvent. A solution of HF/pyridine (70/30) was added drop by drop (0.1 ml/10 mg of reagent). The reaction mixture was stirred a 0° C. for 1 h, then at 25° C. for 6 hours, then extracted with ethyl acetate. The extracts were washed three times with saturated CuSO$_4$ and water and dried over anhydrous MgSO$_4$ to give 0.035 g (0.041 mmol, 48%) of the title product:

$^1$H NMR (CDCl$_3$): δ=1.15 (s, 3H, Me a C-15), 1.23 (s, 9H, 3Me of t-Boc), 1.30 (s, 3H, Me a C-15), 1.42 (s, 3H, Me a C2'), 1.69 (s, 3H, Me a C-8), 1.84 (s, 3H, Me a C-12), 1.89 (m, 1H, H-6β), 2.15 (m, 1H, H-14), 2,25 (s, 3H, Me, OAc of C-10), 2.37 (m, 1H, H-14), 2.55 (m, 1H of C6-H), 2.61 (s, 3H, Me, OAc of C-4), 3.58–3.65 (b, 1H, OH), 3.82 (d, 1H of C3-H, J=7.0 Hz), 4.18 (d, 1H of C20-H J=8.4 Hz), 4.31 (d, 1H of C20-H), 4.42 (dd, 1H of C7-H J$_1$=6.4 Hz, J$_2$=10.8 Hz), 4.95 (dd, 1H of C5-H, J$_1$=2.4 Hz, J$_2$=9.6 Hz), 5.23 (d, 1H, J=9.6 Hz, NH), 5.39 (d, 1H of C3'-H), 5.66 (d, 1H of C2-H), 6,28 (s, 1H, of C10-H), 6.34 (m, 1H, 2-furyl), 6.36 (m, 1H, H-13), 6.38 (m, 1H, 2-furyl), 7.42 (m, 1H, 2-furyl), 7.49 (m, 2H, arom), 7.59 (m, 1H, arom), 8.14 (m, 2H, arom).

EXAMPLE 4

(2'R,3'R)-13-[N-Boc-2-methyl-3-(2-furanyl)isoserinoyl]-14β-hydroxybaccatin III 1,14-carbonate 7-TES-14β-hydroxybaccatin III 1,14-carbonate (0.080 g, 0.125 mmol) was coupled with (3R ,4S)-1-tert-butoxycarbonyl-3-triethylsilyloxy-4-(furan-2-yl)-3-methyl-azetidinone (0.12 g, 0.312 mmol) in the conditions described in example 3c, affording (2'R,3'S)-13-[N-Boc-2-methyl-3-(2-furanyl)isoserinoyl]-3',7-diTES-14β-hydroxybaccatin III 1,14-carbonate (0.087 g, 0.0775 mmol, 62%) was obtained: $^1$H NMR (CDCl$_3$): δ=0.5–0.6 (m, 12H, 6 CH$_2$), 0.85–0.95 (m, 18H, 6 Me), 1.25 (s, 3H, Me), 1.29 (s, 9H, 3Me), 1.31 (s, 3H, Me), 1.56 (s, 3H, Me), 1.75 (s, 3H, Me), 1.92 (m, 1H of C6-H, J$_{6-6'}$=14.3 Hz), 2.02 (s, 3H, Me), 2.20 (s, 3H, Me), 2.51 (m, 1H of C6-H), 2.71 (s, 3H, Me), 3.76 (d, 1H of C3-H, J=8.1 Hz), 4.26 (q, 2H of C20, J=8.5 Hz), 4.44 (m, 1H of C7-H, J$_1$=10.8 Hz, J$_2$=7.0 Hz), 4.85 (d, 1H of C14-H, J=7.0 Hz), 4.89 (m, 1 H of C5-H, J$_1$=1.8 Hz, J$_2$=9.8 Hz), 5.24 (d, 1H, 1H of C3'-H, J=10.0 Hz), 5.28 (d, 1H of NH), 6.10 (d, 1H of C2-H), 6.26 (d, 1H of 2-furyl), 6.38 (m, 1H of 2-furyl), 6.42 (s, 1H of C10-H), 6.47 (d, 1H of C13-H), 7.38 (m, 1H of 2-furyl), 7.42–7.50 (m, 2H, arom), 7.54–7.60 (m, 1H, arom) 8.02–8.08 (m, 2H, arom).

Such a derivative was treated with the HF/pyridine solution to afford the title compound (0.063 g, 0.70 mmol, 91%): $^1$H NMR (CDCl$_2$): δ 1.25 (s, 9H, 3 Me), 1.28 (s, 3H, Me), 1.43 (s, 3H, Me), 1.75 (s, 3H, Me), 1.86 (s, 3H, Me), 1.92 (m, 1H of C6'-H, J$_{6-6'}$=14.3 Hz), 2.24 (s, 3H, Me), 2.55 (m, 1H of C6-H), 2.63 (s, 3H, Me), 3.73 (d, 1H of C3-H, J=8.0 Hz), 4.26 (q, 2H of C20, J=8.5 Hz), 4.38 (m, 1H of C7-H, J$_1$=10.8 Hz, J$_2$=7.0 Hz), 4.86 (d, 1H of C14-H, J=7.0 Hz), 4.93 (m, 1 H of C5-H, J$_1$=1.8 Hz, J$_2$=9.8 Hz), 5.26 (d, 1H, 1H of C3'-H, J=9.5 Hz), 5.44 (d, 1H of NH), 6.12 (d, 1H of C2-H), 6.28 (s, 1H of C10-H), 6.36 (d, 1H of 2-furyl), 6.40 (m, 1H of 2-furyl), 6.47 (d, 1H of C13-H), 7.42 (m, 1H of 2-furyl), 7.44–7.50 (m, 2H, arom), 7.58–7.62 (m, 1H, arom) 8.02–8.08 (m, 2H, arom).

EXAMPLE 5 a) (3R,4R)-3-Hydroxy-1-(4-methoxyphenyl)-3-methyl-4-trifluoromethylazetidin-2?-one A solution of (2S, 5S)-2-tert-butyl-2,5-dimethyl-[1,3]dioxolan-4-one (described in J. Org. Chem., 1999, 64, 4643–4651) (0.344 g, 2.03 mmol) in THF was added with a 1 M solution of LIHMDS (2.4 ml, 2.4 mmol) in THF at –78° C. After 30 min, the solutions of HMPA and N-(4-methoxy phenyl)trifluoroacetaldimine (0.81 g, 4.00 mmol) were added in succession (THF:HMPA=85:15). After 4 h the reaction mixture was treated with 5 ml of a 1M aqueous solution of CH$_3$CO$_2$H at –78° C., extracted with 1N HCl, then with NH$_4$Cl, finally with brine. The organic phase was dried (Na$_2$SO$_4$) and the solvent was evaporated off under reduced pressure. Chromatography of the residue (SiO$_2$, EtOAc/n-pentane, 1:2) afforded 0.25 g (0.91 mmol, 45%) of the title β-lactam (3R,4R): [α]$_D^{20}$=+28.4 (c 1.01, CHCl$_3$); $^1$H NMR (CDCl$_3$): δ=1.70 (d, 3H, Me, J=1.2 Hz), 3.02–3.10 (b, 1H, OH), 3.78 (s, 3H, OMe), 4.33 (q, 1H, J$_{H-F}$=5.7 Hz), 6.85–7.40 (m, 4H, arom); $^{13}$H NMR (CDCl$_3$): δ=22.2 (Me), 55.5 (OMe), 63.9 (q, CH, J=31 Hz), 82.8 (C), 114.4 (2 CH), 119.7 (2 CH), 123.7 (CF$_3$, J=279 Hz), 129.3 (C), 157.3 (C), 167.9 (C).

b) (3R,4R)-3-triethylsilyloxy-1-(4-methoxy-phenyl)-3-methyl-4-trifluoromethyl-azetidin-2-one A solution of compound from a) (0.25 g,. 0.91 mmol) in DMF (3.0 ml) was added with Et$_3$SiCl (0.31 g, 2.0 mmol) and N-methylimidazole (0.28 g, 4 mmol) at 25° C. After 2 hr-stirring the reaction mixture was poured into ice-water, extracted with ethyl acetate and dried. The solvent was evaporated off and the residue was chromatographed to afford 0.32 g (0.82 mmol, 90%) of title product: IR (CDCl$_3$, cm$^{-1}$): 2957, 2878, 1778, 1514, 1298, 1251; $^1$H NMR (CDCl$_3$): δ=0.75 (m, 6H, 3CH$_2$), 0.98 (t, 9H, 3Me), 1.65 (s, 3H, Me), 3.79 (s, 3H, OMe), 4.22 (q, 1H, J$_{H-F}$=5.9 Hz), 6.85–7.40 (m, 4H, arom); $^{13}$H NMR (CDCl$_3$): δ=5.7 (CH$_2$), 6.6 (Me), 23.4 (Me), 55.5 (OMe), 64.3 (q, CH, J=32 Hz), 84.0 (C), 114.4 (2. CH), 119.5 (2 CH), 123.6 (CF$_3$, J=283, Hz), 129.8 (C), 157.1 (C), 167.1 (C).

c) (3R,4R)-3-triethylsilyloxy-3-methyl-4-trifluoromethyl-azetidin-2-one

A solution of compound from b) (0.30 g, 0.77 mmol) in acetonitrile (13.0 ml) was added a drop by drop with ammonium and cerium (IV) nitrate (1.5 g, 2.74 mmol) in water (20.0 ml) and further water (30 ml) in 2 h at –50° C. The mixture was diluted with water (30 ml) and extracted with ethyl acetate. The organic phase was washed with saturated NaHCO$_3$, saturated NaHSO$_3$ and again with saturated NaHCO$_3$. The organic layer was dried and concentrated in vacuo. The residue was subjected to column chromatography (SiO$_2$, CH$_2$Cl$_2$/ethyl acetate, 3:1) to afford the title product (0.168 g, 0.59 mmol, 77%): $^1$H NMR (CDCl$_3$): δ=0.69 (m, 6H, 3 CH$_2$), 0.94 (t, 9H, 3Me), 1.60 (s, 3H, Me), 3.77 (q, 1H, J$_{H-F}$=6.2 Hz), 6.20–6.45 (b, 1H, NH); $^{13}$H NMR (CDCl$_3$): δ=5.8 (CH$_2$), 6.8 (Me), 23.7 (Me), 61.0 (q, CH, J=32 Hz), 86.3 (C), 123.8 (CF$_3$, J=280 Hz), 170.8 (C).

d) (3R,4R)-1-(tert-butoxycarbonyl)-3-triethylsilyloxy-3-methyl-4-trifluoromethyl-azetidin -2-one A solution of compound from c) (0.168.g, 0.59 mmol), DMAP (10 mg) and triethylamine (0.25 ml, 1.77 mmol) in dichloromethane (2.0 ml) at 0° C. was added with a solution of di-tert-butyl dicarbonate (0.32 g, 1.47 mmol) in dichloromethane (1.0 ml). The reaction mixture was stirred at 25° C. for 2 h, then quenched with saturated NH$_4$Cl. The mixture was extracted with ethyl acetate and, the organic layer was washed with brine, dried and concentrated under reduced pressure. Chromatography (SiO$_2$, n-pentane/ethyl acetate, 4:1) afforded 0.210 g (0.56 mmol, 95%) of the title product: $^1$H NMR (CDCl$_3$): δ=0.69 (m, 6H, 3CH$_2$), 0.95 (t, 9H, 3Me), 1.52 (s, 9H, 3Me), 1.63 (s, 3H, Me), 4.10 (q, 1H, J$_{H-F}$=6.2 Hz); $^{13}$H NMR (CDCl$_3$): δ=5.6 (CH$_2$), 6.5 (Me), 23.5 (Me), 27.8 (3 Me), 63.2 (q, CH, J=32 Hz), 84.7 (C), 122.8 (CF$_3$, J=281 Hz), 147.2.(C), 167.4 (C).

e) (2'R,3'R)-13-[N-Boc-2-methyl-3-trifluoromethyli-soserinoyl]-14β-hydroxybaccatin III 1,14-carbonate The reaction of 7-TES-14β-hydroxybaccatin III (0.080 g, 0.11 mmol) with the compound from d) (0.103 g, 0.27 mmol) according to the procedure of example 4 afforded the 7,3'-di-TES-derivative of the title compound (0.071 g, 0.063 mmol, 57%): $^1$H NMR (CDCl$_3$): δ=0.62–0.72 (m, 12H, 6 CH$_2$), 0.88–0.95 (m, 18H, 6 Me), 1.25 (s, 9H, 3 Me), 1.31 (s, 3H, Me), 1.52 (s, 6H, 2Me), 1.63 (s, 3H, Me), 1.90 (m, 1H of C6'-H), 2.00 (s, 3H, Me), 2.19 (s, 3H, Me), 2.48 (m, 1H of C6-H), 2.58 (s, 3H, Me), 3.74 (d, 1H of C3-H, J=7.5 Hz), 4.24 (q, 2H of C20, J=8.8 Hz), 4.41 (m, 1H of C7-H, J$_1$=10.6 Hz, J$_2$=6.4 Hz), 4.74 (m, 1H, C3'-H), 4.83 (d, 1H of C14-H, J=6.9 Hz), 4.86 (m, 1 H of C5-H, J$_1$=1.90 Hz, J$_2$=9.8 Hz), 5.10 (d, 1H of NH), 6.10 (d, 1H of C2-H), 6.40 (s, 1H of C10-H), 6.42 (m, 1H of C13-H), 7.44–7.50 (m, 2H, arom), 7.58–7.60 (m, 1H, arom) 8.06–8.10 (m, 2H, arom). This derivative was treated with the HF/pyridine solution to provide the title compound (0.048 g, 0.54 mmol, 85%): $^1$H NMR (CDCl$_3$): 1.28 (s, 9H, 3 Me), 1.31 (s, 3H, Me), 1.33 (s, 3H, Me), 1.73 (s, 3H, Me), 1.90 (s, 3H, Me), 1.90 (m, 1H of C6'-H), 2.25 (s, 3H, Me), 2.55 (m, 1H of C6-H), 2.57 (s, 3H, Me), 3.736 (d, 1H of C3-H, J=7.6 Hz), 4.26 (q, 2H of C20, J=8.8 Hz), 4.38 (m, 1H of C7-H, J1=10.8 Hz, J2=6.4 Hz), 4.82 (m, 1H, C3'-H), 4.86 (d, 1H of C14-H, J=6.8 Hz), 4.90 (m, 1 H of C5-H, J$_1$=2.3 Hz, J$_2$=9.9 Hz), 5.24 (d, 1H of NH), 6.10 (d, 1H of C2-H), 6.26 (s, 1H of C10-H), 6.47 (d, 1H of C13-H), 7.48–7.54 (m, 2H, arom), 7.58–7.64.(m, 1H, arom) 8.08–8.12 (m, 2H, arom).

EXAMPLE 6

(2'R,3'R)-13-[N-Boc-2-methyl-3-(2-thienyl)isos-erinoyl]-14β-hydroxybaccatin III 1,14-carbonate 7-TES-14β-hydroxybaccatin III 1,14-carbonate (0.24 g, 0.375 mmol) was coupled with (3R,4S)-1-tert-butoxycarbo-nyl-3-triethylsilyloxy-4-(thien-2-yl)-3-methyl-azetidinone (0.36 g, 0.936 mmol) in the conditions described in example 3c.

After the protection with HF/pyridine solution the title compound was obtained as a white solid (0.189 g, 2.1 mmol, 55%): $^1$H NMR (CDCl$_2$): δ 1.25 (s, 9H, 3 Me), 1.28 (s, 3H, Me), 1.43 (s, 3H, Me), 1.75 (s, 3H, Me), 1.86 (s, 3H, Me), 1.92 (m, 1H of C6'-H, J$_{6-6'}$=14.3 Hz), 2.24 (s, 3H, Me), 2.55 (m, 1H of C6-H), 2.63 (s, 3H, Me), 3.73 (d, 1H of C3-H, J=8.0 Hz), 4.26 (q, 2H of C20, J=8.5 Hz), 4.38 (m, 1H of C7-H, J$_1$=10.8 Hz, J$_2$=7.0 Hz), 4.86 (d, 1H of C14-H, J=7.0 Hz), 4.93 (m, 1H of C5-H, J$_1$=1.8 Hz, J$_2$=9.8 Hz), 5.26 (d, 1H, 1H of C3'-H, J=9.5 Hz), 5.44 (d, 1H of NH), 6.12 (d, 1H of C2-H), 6.28 (s, 1H of C10-H), 7.07 (dd, 5.0, 3.6 Hz, H-3 thienyl), 7.16 (dd, 3.6, 1.0, H-4 thienyl), 6.47 (d, 1H of C13-H), 7.35 (dd, 5.0, 1.0, H-5 thienyl), 7.44–7.50 (m, 2H, arom), 7.58–7.62 (m, 1H, arom) 8.02–8.08 (m, 2H, arom).

Pharmacological Experimentation

Pharmacological experimentation was carried out on the compounds of the invention at a 0.1% concentration in dimethylsulfoxide. A2780wt, A2780cis, A2780adr and A2780tax cell lines were used. Cells were plated on 96 well flat bottom plates (Viewplates, Packard). After 24-hours, the culture medium was replaced and, after washing, media containing the tested compounds were added. A dose-response logarithmic curve was established in quadruplicate for each plate, starting from 0.01 to 100000,000 nM. Each assay was effected in duplicate three times. After 72 hour-culture in the presence of the tested compounds, the cells were collected and the number of viable cells was evaluated by ATP dosage, using the ATPlite kit (Packard, Meridien, Mo., USA) and the Topcount (Packard) automated luminometer. For each drug/cell line, the dose-response curve was plotted and the IC50 values were calculated from the concentration-effect curve obtained in three tests with the sigmoid-Emax model using non-linear regression, weighted by the reciprocal of the square of the predicted effect. The resulting IC50 values after continues exposure to the tested compounds for 72 hours are reported in the following table:

TABE

| Compound | A2780wt | A2780cis | A2780tax | A2780adr |
| --- | --- | --- | --- | --- |
| Paclitaxel | 5.3 ± 1.3 | 4.6 ± 0.7 | 4498 ± 123 | 2688 ± 454 |
| Es. 1 | 3.1 ± 0.2 | 2.9 ± 0.1 | 420 ± 93 | 61.4 ± 3.9 |
| Es. 3 | 2.9 ± 0.1 | 3.3 ± 0.2 | 312 ± 61 | 41.3 ± 7.4 |
| Es. 2 | 2.53 ± 1.47 | 1.7 ± 0.4 | 299 ± 77 | 52.9 ± 16.2 |
| Es. 5 | 4.64 ± 2.58 | 2.8 ± 0.6 | 285 ± 60 | 79.3 ± 19.9 |
| Es. 4 | 5.9 ± 0.7 | 2.5 ± 0.3 | 30.9 ± 3.7 | 27.1 ± 10.1 |
| Es. 6 | 3.7 ± 0.4 | 2.9 ± 0.2 | 160.4 ± 32 | 93.2 ± 20.4 |

The invention claimed is:
1. Compounds of formula (I):

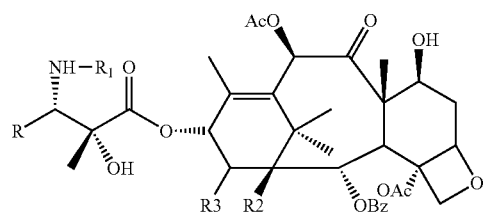

in which:
R is trifluoromethyl, phenyl, 2-furyl, 2-thienyl;
R$^1$ is t-butoxycarbonyl or benzoyl;
R$_2$ is hydroxy;
R$_3$ is hydrogen or, together with R$_2$, it forms the residue of a cyclic carbonate of formula:

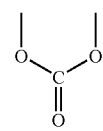

with the proviso that when R$_3$ is hydrogen,
R is different from phenyl.
2. As compounds of formula (I):
(2'R,3'R)-13-[N-benzoyl-3-(2-furyl)-2-methyl-isos-erinoyl]-baccatin III;
(2'R,3'R)-13-[N-t-butoxycarbonyl-3-(2-furyl)-2-methyl-isoserinoyl]-baccatin III;

(2'R,3'S)-13-[N-t-butoxycarbonyl-3-phenyl-2-methyl-isoserinoyl]-14-hydroxybaccatin III 1,14-carbonate;

(2'R,3'R)-13-[N-t-butoxycarbonyl-3-trifluoromethyl-2-methyl-isoserinoyl]-14-hydroxybaccatin III 1,14-carbonate;

(2'R,3'R)-13-[N-t-butoxycarbonyl-3-(2-furyl)-2-methyl-isoserinoyl]-14-hydroxybaccatin III 1,14-carbonate.

(2'R,3'R)-13-[N-t-butoxycarbonyl-3-(2-thienyl)-2-methyl-isoserinoyl]-14-hydroxybaccatin III 1,14-carbonate.

3. Pharmaceutical compositions containing one of the compounds of formula (I), together with pharmaceutically acceptable carriers and excipients.

4. The method of using the compound of formula (I) for the preparation of a medicament with antitumor activity comprising adding an effective amount of the compound to a pharmaceutically acceptable carrier.

* * * * *